(12) United States Patent
Bagaoisan et al.

(10) Patent No.: US 6,270,477 B1
(45) Date of Patent: *Aug. 7, 2001

(54) CATHETER FOR EMBOLI CONTAINMENT

(75) Inventors: Celso J. Bagaoisan, Union City; Hung V. Ha; Mukund R. Patel, both of San Jose; Gholam-Reza Zadno-Azizi, Newark, all of CA (US)

(73) Assignee: PercuSurge, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/813,023

(22) Filed: Mar. 6, 1997

Related U.S. Application Data

(63) Continuation-in-part of application No. 08/650,464, filed on May 20, 1996, now abandoned.

(51) Int. Cl.$^7$ ............................ A61M 29/00; A61M 25/00
(52) U.S. Cl. ...................... 604/96.01; 604/97.01; 604/102.01; 604/527; 606/192
(58) Field of Search ................................ 604/280, 282, 604/264, 96, 532, 523–27, 101, 103, 103.06; 606/192–196

(56) References Cited

U.S. PATENT DOCUMENTS

| 3,144,868 | 8/1964 | Jascalevich . |
| 4,405,313 | 9/1983 | Sisley et al. . |
| 4,445,892 | 5/1984 | Hussein et al. . |
| 4,468,216 | 8/1984 | Muto . |
| 4,481,323 | * 11/1984 | Sterling ............................... 524/269 |
| 4,511,354 | 4/1985 | Sterling . |
| 4,573,966 | 3/1986 | Weikl et al. . |
| 4,619,643 | 10/1986 | Bai . |
| 4,782,834 | 11/1988 | Maguire et al. . |
| 4,790,812 | 12/1988 | Hawkins, Jr. et al. . |
| 4,790,813 | 12/1988 | Kensey . |
| 4,921,483 | 5/1990 | Wijay et al. . |
| 4,946,466 | 8/1990 | Pinchuk et al. . |
| 4,950,238 | 8/1990 | Sullivan . |
| 4,964,409 | 10/1990 | Tremulis . |
| 5,019,057 | 5/1991 | Truckai . |
| 5,027,812 | 7/1991 | Shapiro et al. . |
| 5,059,178 | 10/1991 | Ya . |
| 5,071,405 | * 12/1991 | Piontek et al. .......................... 604/96 |

(List continued on next page.)

FOREIGN PATENT DOCUMENTS

| WO9320881 | 10/1993 | (WO) . |
| WO9508364 | 3/1995 | (WO) . |
| WO 96/15824 | 5/1996 | (WO) . |

*Primary Examiner*—Angela D. Sykes
*Assistant Examiner*—Patricia Bianco
(74) *Attorney, Agent, or Firm*—Knobbe, Martens, Olson & Bear, LLP

(57) ABSTRACT

Disclosed herein is a catheter for use in an emboli containment system. In one embodiment, the catheter has a tubular body with a metallic braid construction. Two lumen extend through the tubular body, the lumen being in a side-by-side configuration. One of the lumen functions as an inflation lumen, and is in fluid communication with an inflatable balloon mounted on the distal end of the catheter. The second lumen is adapted to receive other therapeutic catheters which comprise the emboli containment system.

54 Claims, 5 Drawing Sheets

U.S. PATENT DOCUMENTS

| | | |
|---|---|---|
| 5,087,247 | 2/1992 | Horn et al. . |
| 5,108,419 | 4/1992 | Reger et al. . |
| 5,135,484 | 8/1992 | Wright . |
| 5,158,540 | 10/1992 | Wijay et al. . |
| 5,163,905 | 11/1992 | Don Michael . |
| 5,163,906 | 11/1992 | Ahmadi . |
| 5,167,239 | 12/1992 | Cohen et al. . |
| 5,195,955 | 3/1993 | Don Michael . |
| 5,217,440 | 6/1993 | Frassica . |
| 5,250,060 | 10/1993 | Carbo et al. . |
| 5,257,974 | 11/1993 | Cox . |
| 5,322,508 | 6/1994 | Viera . |
| 5,329,942 | 7/1994 | Gunther et al. . |
| 5,344,402 | 9/1994 | Crocker . |
| 5,346,471 | 9/1994 | Raulerson . |
| 5,370,617 | 12/1994 | Sahota . |
| 5,378,237 | 1/1995 | Boussignac et al. . |
| 5,395,311 | 3/1995 | Andrews . |
| 5,403,274 | 4/1995 | Cannon . |
| 5,423,742 | 6/1995 | Theron . |
| 5,425,709 | 6/1995 | Gambale . |
| 5,439,000 | 8/1995 | Gunderson et al. . |
| 5,449,343 | 9/1995 | Samson et al. . |
| 5,462,529 * | 10/1995 | Simpson et al. ............ 604/101 |
| 5,470,322 | 11/1995 | Horzewski et al. . |
| 5,484,412 * | 1/1996 | Pierpont ........................ 604/101 |
| 5,500,180 | 3/1996 | Anderson et al. . |
| 5,522,800 | 6/1996 | Crocker . |
| 5,527,325 | 6/1996 | Conley et al. . |
| 5,531,721 | 7/1996 | Pepin et al. . |
| 5,533,987 * | 7/1996 | Pray et al. .................... 604/280 |
| 5,536,250 | 7/1996 | Klein et al. . |
| 5,782,811 * | 7/1998 | Samson et al. ............... 604/282 |
| 5,833,644 * | 11/1998 | Zadno-Azizi et al. ......... 604/52 |
| 5,868,705 * | 2/1999 | Bagaoisan et al. ............ 604/96 |
| 5,868,706 | 2/1999 | Cox . |
| 5,891,090 * | 4/1999 | Thornton ...................... 604/102 |

* cited by examiner

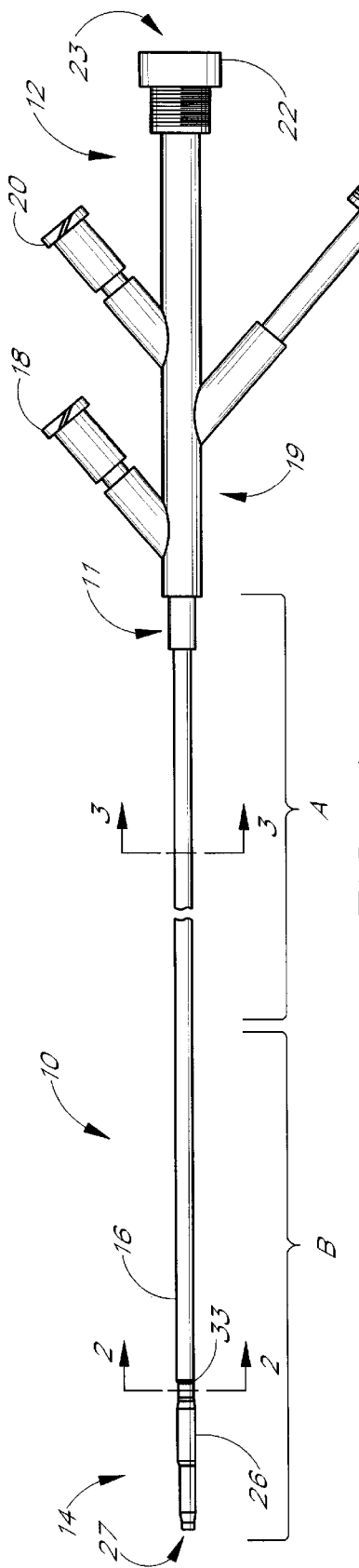
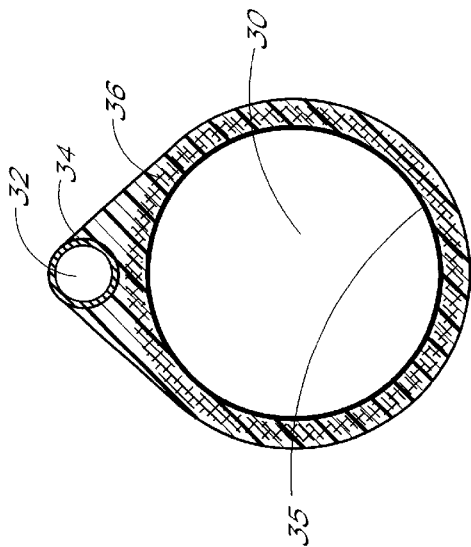
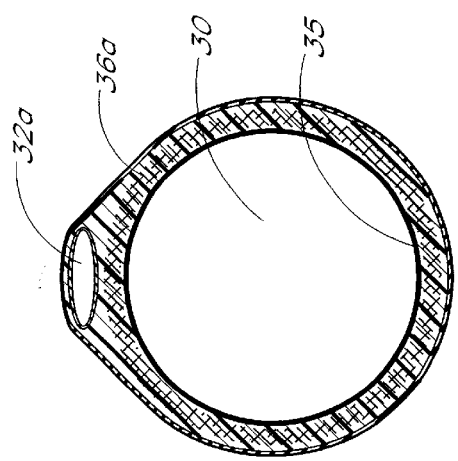

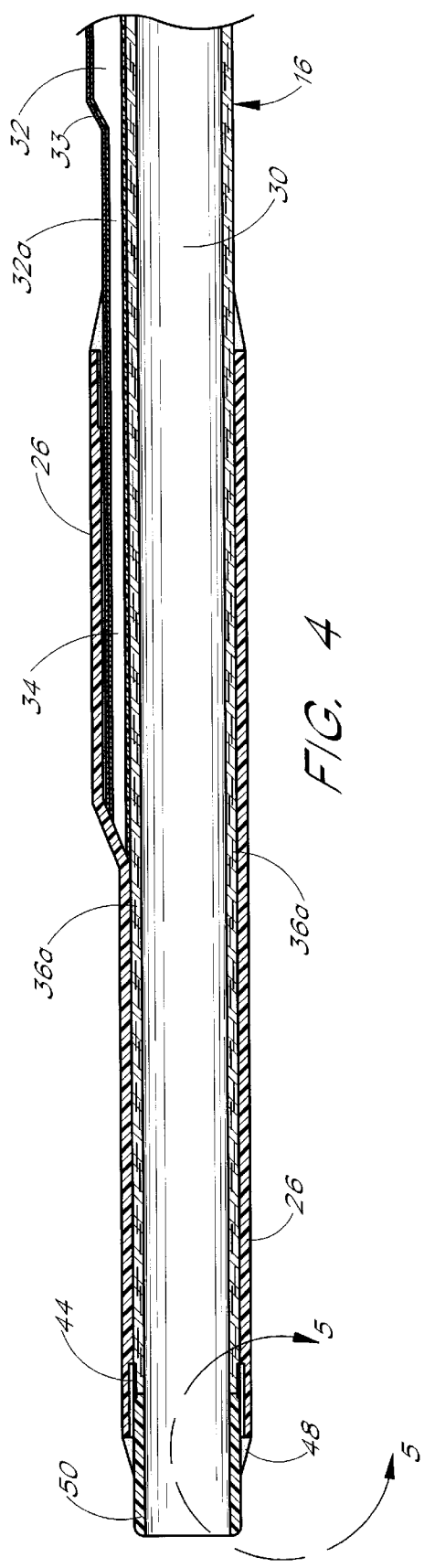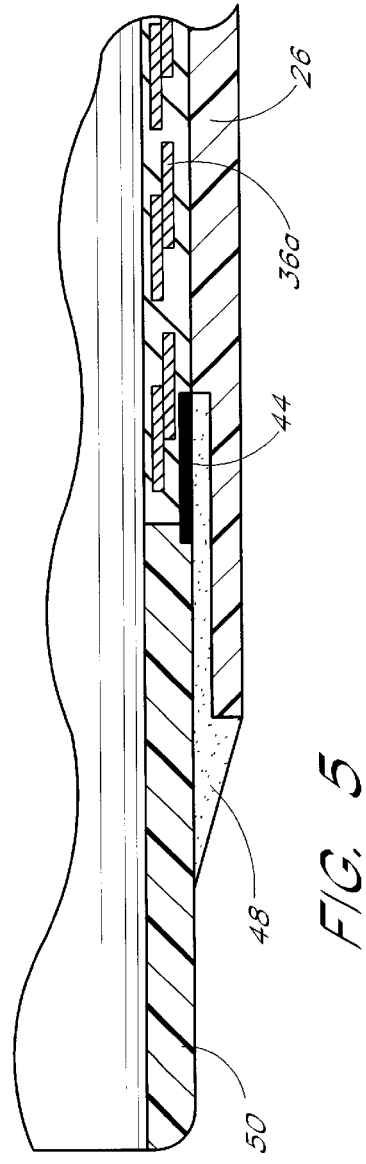

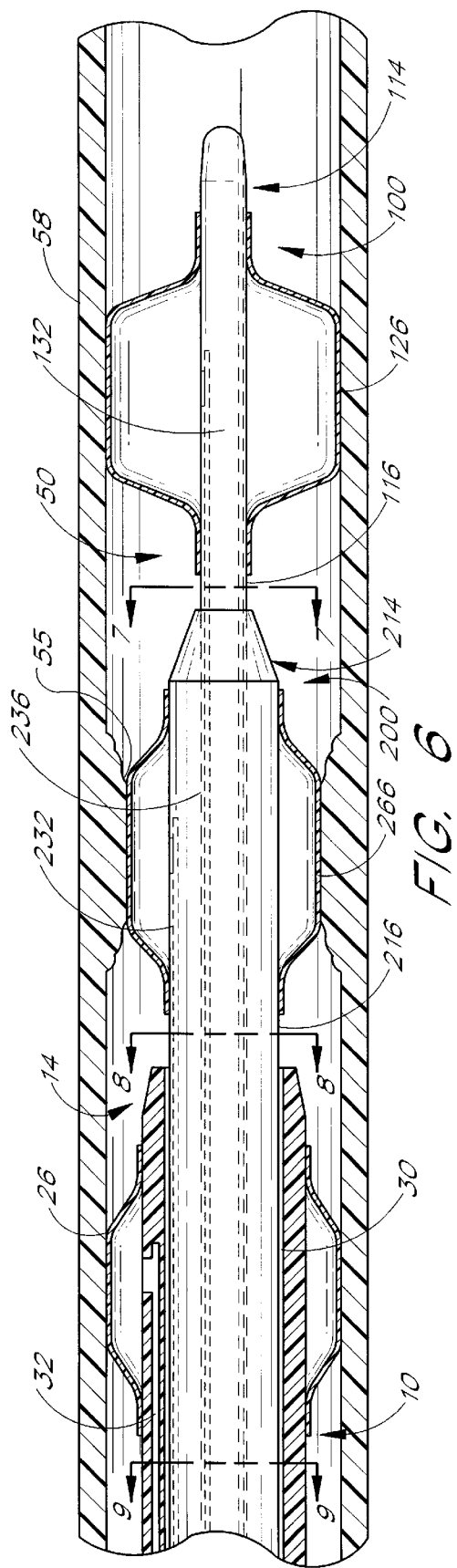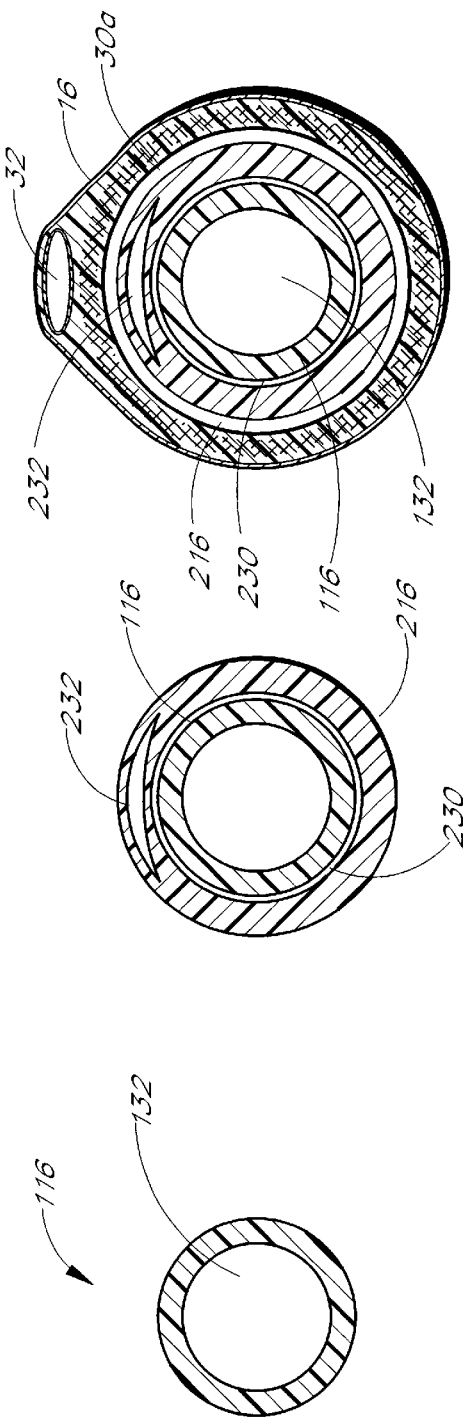

CATHETER FOR EMBOLI CONTAINMENT

CROSS REFERENCE TO RELATED APPLICATION

This application is a continuation-in-part of application Ser. No. 08/650,464 filed on May 20, 1996, the entirety of which is incorporated herein by reference.

BACKGROUND OF THE INVENTION

The present invention generally relates to medical devices, and in particular, to catheters which can be used in an emboli containment system.

Balloon angioplasty, and other transluminal medical treatments, are well-known, and have been proven efficacious in the treatment of stenotic lesions in blood vessels. The application of such medical procedures to certain blood vessels, however, has been limited, due to the risks associated with creation of emboli during the procedure. For example, angioplasty is not the currently preferred treatment for lesions in the carotid artery, because of the possibility of dislodging plaque from the lesion, which can enter the various arterial vessels of the brain and cause permanent brain damage. Instead, surgical procedures are currently used, but these procedures present substantial risks.

One solution to this problem is the use of a multi-catheter emboli containment system, as disclosed in the above-referenced application Ser. No. 08/650,464. As disclosed therein, a treatment chamber within a blood vessel is formed by two occlusion balloons on opposite sides of a stenotic lesion, thereby preventing emboli migration during the treatment procedure. The chamber is created by two occlusion balloon catheters which are slidably disposed with respect to one another.

Emboli containment procedures of this type are advantageous, because they permit the clinician to utilize the benefits of transluminal treatment in a wider variety of blood vessels. However, the procedures require the complex coordination of multiple catheters. Consequently, it is desirable to have catheters which make it easier for the clinician to utilize an emboli containment system. It is also desirable that the catheters used in the emboli containment system have a high degree of flexibility, to navigate tortuous blood vessel networks.

Consequently, there exists a need for improved emboli containment catheters. This is especially true in the context of the "main" catheter, through which other catheters are inserted and controlled to form the emboli containment system.

SUMMARY OF THE INVENTION

The present invention advantageously provides as a main catheter an occlusive device adapted for use in a multi-catheter emboli containment system. In one aspect of the present invention, there is provided a catheter, comprising an elongate flexible tubular body having a proximal end and a distal end. The tubular body incorporates a metallic member, which may comprise a braid or a coil. A main lumen and an inflation lumen extend through the tubular body, and are in a side-by-side configuration. The main lumen is sized to receive a therapeutic and/or diagnostic device such as a balloon angioplasty catheter or an atherectomy catheter. The tubular body is provided with a manifold. The manifold has an aspiration port which is in fluid communication with the main lumen. The distal end of the tubular body also has a tip formed of a more flexible material than that used to form the tubular body.

In one preferred embodiment, an inflatable balloon is mounted on the distal end of the tubular body. An inflation port is also provided on the manifold in this embodiment. The inflation port is in fluid communication with the inflation lumen. In this embodiment, the inflatable balloon is formed of a block copolymer of styrene-ethylene-butylene-styrene.

In another preferred embodiment, the metallic braid or coil is formed of a metal selected from the group consisting of 304, 316, or 400 series stainless steel, nitinol, platinum, gold, Elgiloy (TM), or combinations thereof. Where a metallic braid is used, it may optionally have a braid density at a first point on the tubular body that is greater than the braid density of the metallic braid at a second point on the tubular body by at least 20 picks per inch. Similarly, where a metallic coil is used, it may optionally have a coil density at a first point on the tubular body that is greater than the coil density at a second point on the tubular body.

In another aspect of the present invention, there is provided a catheter comprising an elongate flexible tubular body having a proximal end and a distal end. Alternatively, there may be provided a circular cross-sectional configuration at the proximal end which is continuous with a distal end having a reduced internal and outer tubular body diameters. A first and second lumen extend through the tubular body from the proximal end to the distal end in a side-by-side configuration. The first lumen has a generally circular cross-sectional configuration at the proximal end and a generally oval cross-sectional -configuration at the distal end. The second lumen has a diameter no smaller than 0.05 inches, preferably no smaller than 0.08 inches, and is adapted to slidably accommodate a therapeutic or diagnostic device.

In one preferred embodiment, an inflatable balloon is mounted on the distal end of the tubular body. The inflatable balloon is in fluid communication with the first lumen, such that fluid passing through the first lumen may be used to inflate or deflate the inflatable balloon. The second lumen size may vary in certain embodiments, such that in one embodiment, the second lumen has a diameter no smaller than about 0.05 inches, and is preferably no less than 0.080 inches.

In another aspect of the present invention, there is provided a catheter with variable stiffness, comprising a tubular body having a proximal end and a distal end. A metallic braid or metallic coil is within the tubular body. In one embodiment, the proximal end of the tubular body has a lower braid or coil density than the distal end. In another embodiment, the braid or coil density is kept constant along the length of the tubular body, and the tubular body is formed of materials with greater stiffness at the proximal end. In another embodiment, a combination of braids and coils of varying density can be used at various points along the tubular body, to create a catheter tubular body having a more flexible distal end.

In another aspect of the present invention, there is provided a method of making a catheter tubular body. The method comprises providing a first polymeric tube formed of a first material having a first melting point. The first polymeric tube is then inserted into a second polymeric tube to form a combined tube. The second polymeric tube is formed of a second material having a second melting point which is less than the first melting point. The combined tube is then placed adjacent to a third tube. The third tube is formed in part of the second material. The tubes are then heated to a temperature greater than the second melting point but less than the first melting point, such that the combined tube melt fuses with third tube to form a catheter tubular body having two lumen extending therethrough in a side-by-side configuration. The first material may be selected from the group comprising polyimide, polyamide, PET and PEEK, blends thereof and the second material may be selected from the group comprising Pebax (TM), polyethylene, nylon, or Hytrel (TM) or blends thereof Preferably, the temperature of the heating step is from about 250° to 600° F. It is also preferred that the third tube incorporate a metallic member, such as a braid or coil.

BRIEF DESCRIPTION OF THE DRAWINGS

FIG. 1 is a side view of an embodiment of the catheter of the present invention.

FIG. 2 is a cross-sectional view of catheter of FIG. 1 along lines 2—2.

FIG. 3 is a cross-sectional view of the catheter of FIG. 1 along lines 3—3.

FIG. 4 is a longitudinal cross-sectional view of the distal end of the catheter of FIG. 1.

FIG. 5 is an enlargement of the region circumscribed by lines 5—5 of the catheter of FIG. 4.

FIG. 6 is an illustration of the catheter of the present invention as used in an emboli containment system.

FIG. 7 is a cross-sectional view of the emboli containment system of FIG. 6 along lines 7—7.

FIG. 8 is a cross-sectional view of the emboli containment system of FIG. 6 along lines 8—8.

FIG. 9 is a cross-sectional view of the emboli containment system of FIG. 6 along lines 9—9.

DETAILED DESCRIPTION OF THE PREFERRED EMBODIMENT

Figure 10A:
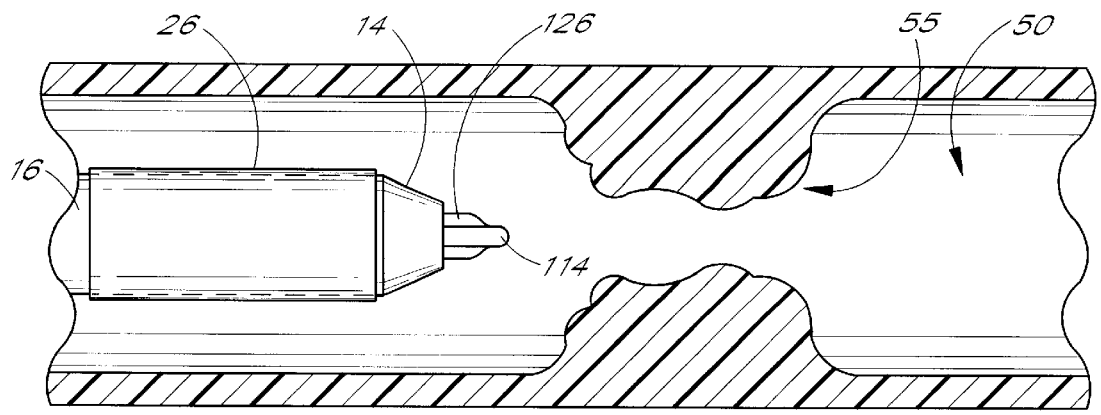
FIGS. 10A–E illustrate the use of an embodiment of the catheter of the present invention in an emboli containmnent treatment procedure.

Referring to FIG. 1, there is depicted an embodiment of the balloon catheter of the present invention. Although illustrated and described below in the context of an emboli containment system featuring balloon dilation treatment of a stenotic lesion, it is to be understood that the present invention can be easily adapted to a variety of emboli containment treatment applications. For example, the present inventors contemplate that the catheter of the present invention can be used in emboli containment treatment procedures which include atherectomy, stent implantation, drug delivery, as well as other applications. Furthermore, although depicted and described as a two lumen catheter, it should be appreciated that the present invention may also be adapted to catheters having more than two lumen. The manner of adapting the present invention to these various treatments and structures will become readily apparent to those of skill in the art in view of the description which follows.

Catheter 10 generally comprises an elongate flexible tubular body 16 extending between a proximal control end 12 and a distal functional end 14. Tubular body 16 has a main lumen 30 which extends between ends 12 and 14. Main lumen 30 terminates in a proximal opening 23 and a distal opening 27. A smaller inflation lumen 32, configured in a side-by-side relationship with main lumen 30, extends along the length of tubular body 16 and may terminate within or near an occlusion balloon 26 mounted on the distal end 14 of catheter 10, as described below. Inflation lumen 32 is in fluid communication with balloon 26, such that fluid passing through inflation lumen 32 may be used to inflate or deflate balloon 26. In some embodiments, the inflation lumen may originate at a point distal to the proximal end 12, and extend distally from that point in a side-by-side configuration with main lumen 30.

In some embodiments, instead of an occlusion balloon 26, distal end 14 is provided with a mechanical occlusive device such as a pull-wire activated braid which filters all particles larger than 12 microns. Alternatively, other occlusive filtering devices may also be used, as is known by those of skill in the art.

A control manifold 19 is provided at the proximal end 12 of catheter 10. Control manifold 19 is generally provided with a number of ports to provide access to the catheter lumen. For example, for the embodiment depicted in FIG. 1, control manifold 19 is provided with a catheter end-access port 22 and a catheter side-access port 24, to provide an introduction point for the insertion of other catheters into lumen 30. Ports 22 and 24 are preferably provided with standard Touhy Borst connectors, although other sealing type connectors, such as a hemostasis valve, may be used. Manifold 19 is also provided with an aspiration port 20 which is in fluid communication with lumen 30, for attachment of devices to aspirate fluid into opening 27, through lumen 30, and out port 20. An inflation port 18, in fluid communication with lumen 32, is further provided on manifold 18 for attachment of devices to inflate or deflate balloon 26. In one preferred embodiment, ports 18 and 20 are provided with standard luer connectors, to facilitate attachment of standard inflation or aspiration apparatus, respectively, to ports 18 and 20. Other embodiments of catheter 10 may feature more or less ports, depending upon the number of lumen in the catheter and the desired functionalities of the catheter.

Manifold 19 is preferably formed out of hard polymers or metals, which possess the requisite structural integrity to provide a functional access port to the catheter lumen, such as for balloon inflation or fluid aspiration. In one preferred embodiment, manifold 19 is integrally formed out of medical grade polycarbonate. Other suitable materials may be used to form manifold 19, such as polyvinyl chloride, acrylics, acrylonitrile butadiene styrene (ABS), nylon, and the like.

Manifold 19 is attached to tubular body 16 so that the various ports are placed in communication with the appropriate lumen, as described above in connection with FIG. 1. Preferably, a strain relieving connector 11 is used to join manifold 19 to tubular body 16. For the embodiment depicted in FIG. 1, strain relieving connector 11 consists of a length of flexible polymeric tubing, such as 40 durometer (D) Pebax (TM), or other polyether block amides, and other similar materials. Tubular body 16 is inserted in one end of strain relieving connector 11, and the other end of strain relieving connector 11 is inserted into manifold 19. Suitable adhesives, such as a cyanoacrylate, epoxies, or uv curable adhesives, may be used to bond manifold 19 to strain relieving connector 11. Alternately, manifold 19 may also be insert molded with the tubular body 16, as is known by those of skill in the art. Adhesives may also be used to bond the strain relieving connector 11 to tubular body 16, or alternately, conventional heat bonding, as known to those of skill in the art, may be used to attach tubular body 16 to strain relieving connector 11.

The length of tubular body 16 may be varied considerably depending upon the desired application. For example, where catheter 10 is to be used as part of an emboli containment system for treatment of carotid artery disease, with catheter 10 being introduced at the groin, the length of tubular body 16 may range from 80 to 110 centimeters, and is preferably 95 cm. Other treatment procedures, requiring a longer or shorter tubular body 16, are easily accommodated by the present invention, by forming a tubular body 16 of the desired length during the manufacturing process.

The outer diameter of tubular body 16 may also be varied considerably, and in most cases, will depend upon the intended treatment procedure for which catheter 10 will be used. That is, the outer diameter of tubular body 16 must be large enough to be capable of forming a main lumen 30 which can slidably accommodate the other catheters used in the emboli containment system, as described in detail below. However, the outer diameter of tubular body 16 must also be smaller than the internal diameter of smallest blood vessel through which catheter 10 passes during the selected treatment procedure. In general, the diameter of main lumen 30 may range from at least about 0.05 inches to about 0.12 inches, and be capable of accommodating many types of catheters to be used therein, while still maintaining a low profile for the diameter of tubular body 16.

For many treatment applications, it has been found that a tubular body having an outside diameter of no more than about 0.135 inches (10 French) is preferred. Advantageously, with an outer diameter of this size, main lumen 30 may have an internal diameter of about 0.10 inches, making lumen 30 capable of accommodating a wide variety of treatment catheters, or catheters used for diagnostic purposes. Of course, as will be appreciated by those of skill in the art, where the catheters intended to be inserted into lumen 30 are known to have outer diameters significantly smaller than 0.10 inches, such that lumen 30 may be smaller than 0.10 inches and still accommodate them, a tubular body 16 having an outer diameter of less than 0.135 inches may be selected.

Although not required, the interior surface of lumen 30 may be provided with a liner 35 formed of a lubricous material, to reduce the frictional forces between the lumen surface and the catheters which are inserted into lumen 30. In one preferred embodiment, liner 35 is formed out of polytetrafouoroethylene (PTFE). Lubricous materials other than PTFE, which are biocompatible, fairly flexible, and easily mounted to other polymeric materials of the type used to form catheter tubular bodies, may also be used to form liner 35. Examples of such materials include polyethylene, Pebax (TM), nylon, and the like. Where increased flexibility of the distal end 14 of catheter 10 is desired, Pebax (TM) may be used in place of PTFE along a selected portion of distal end 14, such as the distal most 15–20 cm of end 14.

To minimize the outer diameter of tubular body 16, it is preferable that inflation lumen 32 be as small as possible in accordance with its function. That is, inflation lumen 32 is preferably no larger than required to provide sufficient fluid to balloon 26 for rapid inflation, or so that fluid may be quickly withdrawn from balloon 26 during deflation. For compliant expansion balloons of the type described below, inflation lumen diameters of from about 0.008 inches to about 0.018 inches are satisfactory, with a diameter of about 0.014 inches being preferred for some applications.

Furthermore, in one embodiment, as illustrated in FIGS. 1–3, the outer diameter of tubular body 16 just proximal to balloon 26 is minimized by providing an inflation lumen 32a with an oval cross-sectional configuration, as illustrated in FIG. 3. Preferably, inflation lumen 32a has an oval cross-sectional configuration which extends proximally from the proximal edge balloon 26 by a distance of at least 0.1 cm, more preferably 1 cm, and optimally by a distance equal to the length of tubular body 16. For ease of manufacturing, the cross-sectional configuration of lumen 32 at points further proximal to balloon 26 may be generally circular, as illustrated in FIG. 2. Where the lumen configuration differs from proximal to distal end, as illustrated in FIGS. 2 and 3, a region of transition 33 is provided wherein the lumen configuration changes from circular to oval.

It will be appreciated by those of skill in the art that other cross-sectional configurations of lumen 32a may be provided and still function to reduce the profile of tubular body 16. For example, triangular, rectangular, or other non-oval cross sectional configurations are easily adapted to lumen 32a, and the manner of incorporating such alternative cross-sectional configurations will be readily apparent to those of skill in the art in view of the description which follows.

A variety of different manufacturing methods may be used to alter the cross-sectional configuration of lumen 32, as will be appreciated by those of skill in the art. In one preferred method, lumen 32 is formed of a polymeric tube, such as a polyimide tube, which has been compressed at one end so that it has the desired oval shape. The polyimide tube is then inserted into a second tube formed of a material having a lower melting point than polyimide, such as 72D Pebax (TM). The combination is then heat bonded to another tube defining main lumen 30, such as a braided Pebax (TM) tube, as described below. The heat bonding takes place at a temperature greater than the melting temperature of Pebax (TM), but less than the melting temperature of polyimide, so that the Pebax (TM) tubes melt fuse to form the two lumen tubular body.

Alternately, the cross-sectional configuration, as well as the cross-sectional area of lumen 32, may also be altered by joining two separate polymeric tubes together to form a continuous inflation lumen 32. One of the tubes, corresponding to the proximal end of catheter 10 as shown in FIG. 3, may have a circular cross-sectional configuration. The second tube, corresponding to the distal end of catheter 10 as shown in FIG. 2, has an oval configuration. One end of a mandrel may be inserted into each of the tubes, and conventional heat bonding may be used to create the cross-sectional configuration transition. As before, the combined tube may then be heat bonded to a second tube defining main lumen 30 to form tubular body 16.

As illustrated in FIG. 1, an inflatable balloon 26 is mounted on the distal end 14 of catheter 10. In most applications where catheter 10 is to be used in an emboli containment treatment procedure, inflatable balloon 26 will function as an occlusion balloon, to prevent blood from passing through the blood vessel distal of balloon 26. Thus, inflatable balloon 26 is preferably able to expand to fit a variety of different blood vessel diameters. Accordingly, it is preferred that inflatable balloon 26 have a compliant expansion profile, tending to increase in radial diameter with increasing inflation pressure. To achieve this, balloon 26 may be made out of materials which impart such expansion characteristics, including elastomeric materials such as latex or silicone. In one preferred embodiment, inflatable balloon 26 is formed out of a material comprising a block copolymer of styrene-ethylene-butylene-styrene, sold under the trade name C-Flex (TM). Further details as to balloons of this type are disclosed in our copending application entitled PRE- STRETCHED CATHETER BALLOON, Ser. No. 08/812, 140, filed on the same date as the present application, the entirety of which is incorporated by reference.

Inflatable balloon 26 may be placed in fluid communication with lumen 32a via a fill hole (not shown) extending through tubular body 16 within balloon 26, such that fluid may be introduced into lumen 32 through inflation port 18 to inflate balloon 26. Alternately, lumen 32a may terminate within balloon 26, to provide the requisite fluid communication. Balloon 26 may be attached to tubular body 16 by any suitable manner known to those of skill in the art, such as adhesives or heat bonding.

Tubular body 16 must have sufficient structural integrity, or "stiffness," to permit catheter 10 to be advanced through vasculature to distal arterial locations without buckling or undesirable bending of tubular body 16. However, it is also desirable for tubular body 16 to be fairly flexible near distal end 14, so that tubular body 16 may be navigated through tortuous blood vessel networks. Thus, in one preferred embodiment, tubular body 16 is made to have variable stiffness along its length, with the proximal portion of tubular body 16 being less flexible than the distal portion of tubular body 16. Advantageously, a tubular body 16 of this construction enables a clinician to more easily insert tubular body 16 into blood vessel networks difficult to reach by a tubular bodies having uniform stiffness. This is because the stiffer proximal portion provides the requisite structural integrity needed to advance tubular body 16 without buckling, while the more flexible distal region is more easily advanced into and through tortuous blood vessel passageways.

In one preferred embodiment, variable stiffness along the length of tubular body 16 is achieved by forming a polymeric tubular body 16 which incorporates along its length a variable stiffness metallic member. The metallic member may comprise a braid or coil, and may have varying braid density or coil pitch at different points along the catheter tubular body. For example, as shown in FIGS. 2 and 3, tubular body 16 may be provided with a braid 36 incorporated into the wall structure of tubular body 16. Referring to FIG. 1, to achieve variable stiffness, proximal region A of catheter 10 is provided with a metallic braid 36 having a lower braid density than that present in the metallic braid 36a of distal region B. The lower braid density of proximal region A permits polymer flow in between the braids during the formation of the tubular body. Because the polymer is relatively stiffer than the braid, the lower braid density results in proximal region A being less flexible, or "stiffer", than distal region B. In one preferred embodiment, the braid density of proximal region A varies from 60 to 80 picks per inch, while that of region B varies from 90 to 110 picks per inch.

As will be appreciated by those of skill in the art, metallic members other than braids may be incorporated into tubular body 16 to create variable stiffness. For example, a metallic coil may be introduced into tubular body 16. The coil may have different pitch along the length of tubular body 16, such that region A is provided with a coil having a lower pitch than that present in region B. The manner of adapting a coil, and other metallic members, to the catheter tubular body in place of a braid will become readily apparent to those of skill in the art in view of the description which follows.

The precise density of the braiding provided to regions A and B can be varied considerably at the point of manufacture, such that catheters having a variety of different flexibility profiles may be created. Moreover, the braid density may be varied within catheter regions A and B as well, by providing a metallic braid which has a braid density gradient along its length For example, the most proximal part of region A may be provided with a metallic braid 36 having a braid density of about 60 picks per inch, with the braid density increasing distally at a certain rate so that the final pick count is not more than 110 picks per inch at the distal end.

A variety of different metals, known to be ductile and shapeable into fine wires and flat ribbons, having a diameter of about 0.0005 inches to about 0.005 inches for wires, or the same thickness for a ribbon, may be used to form the metallic braids 36 and 36a or metallic coils. For example, stainless steel, platinum, gold and nitinol, or combinations thereof are all suitable metals. In one preferred embodiment, braid 36 is formed of stainless steel, and has a braid density which varies from 70 picks per inch at the most proximal part of region A, to 100 picks per inch at the most distal part of region B.

Metallic braids 36 may be introduced into the structure of tubular body 16 through conventional catheter forming techniques. For example, tubular body 16 may be formed by braiding over a 72D Pebax (TM) tube that has a removable core mandrel in the internal diameter supporting the Pebax (TM) tube, and then inserting the braided tube into a 72D Pebax (TM) outer tube at the proximal region A and a 35D Pebax (TM) tube at the distal region B, so that the braid is sandwiched between the inner and outer tubes. A stainless steel support mandrel may be inserted into the removable core mandrel as additional support. A shaping container such as a fluorinated ethylene propylene (FEP) shrink tube is inserted over the outer Pebax (TM) tube, and the entire apparatus may then be placed in a hot box or oven kept at a temperature slightly greater than the melting temperature of the Pebax (TM) tubes. The Pebax (TM) tubes will melt and fuse together, and once cooled, will form a tubular body incorporating the metallic braid. The shaping container and mandrels may then be removed and discarded.

In another embodiment, variable stiffness of tubular body 16 may be achieved by forming regions A and B of tubular body 16 out of polymeric materials having differing degrees of stiffness. For example, one half of an inner tube of 72D Pebax (TM) may be inserted into an outer tube of 35D Pebax (TM), and the other half of the inner tube may be inserted into a 72D Pebax (TM) outer tube. The combination may then be heat fused, as described above. The 35D/72D Pebax (TM) combination forms a more flexible tubular body than the region 72D/72D Pebax combination. More or less flexible materials may be used as desired to alter the flexibility of the resulting tubular body. Furthermore, the flexibility of the various regions of a tubular body formed in this manner may be varied further by incorporating a metallic member having either a uniform density, or a varying density, into the tubular body, as described above.

In another preferred embodiment, variable stiffness along the length of the tubular body may be achieved by using different metallic members in regions A and B. For example, proximal region A may be provided with a multilayer coil, while distal region B may be provided with a braid. Alternately, proximal region A may be provided with a metallic braid, while distal region B may be provided with a single layer coil. As discussed above, the densities of the metallic members in the respective sections may be varied considerably to select for a desired variable stiffness profile, as will be appreciated by those of skill in the art.

In one preferred embodiment, variable stiffness along the length of the tubular body is achieved by keeping the braid density constant along the length of tubular body 16 and then forming the proximal and distal portions of tubular body 16 of polymeric materials of differing stiffness. For example, braid density may be uniform and range from 60–80 pick/ inch, more preferably be about 70 picks/inch, with region A being formed of 72D Pebax (TM) and region B being formed of 25-50D Pebax (TM). Alternately, region A can be formed of high density polyethylene and region B of low density polyethylene.

Moreover, any of a variety of different polymeric materials known by those of skill in the art to be suitable for catheter body manufacture may be used to form tubular body 16. For example, tubular body 16 may be formed out of Pebax (TM), blends of Pebax (TM), and nylons, polyetheretherketone (PEEK), polyethylenes, and Hytrel (TM), and the like. Different materials might also be combined or blended to select for desirable flexibility properties.

Also, although tubular body 16 has been described in the context of having two regions of differing flexibility, it will be readily appreciated by those of skill in the art that three or more regions of differing flexibility may easily be provided, by adapting the teachings contained herein.

In the above-discussed embodiments, and all other embodiments of the present invention, it may be preferred to provide main lumen 30 and the outer surface of tubular body 16 with a hydrophilic coating, a hydrophobic coating, or combinations thereof. For example, main lumen 30 may be provided with a hydrophobic coating, such as silicone, while tubular body 16 is provided with a hydrophillic coating, such as polyvinyl pyrrolidone (PVP), polyurethane blends, copolymers of acrylonitrile, and the like. Other hydrophobic and hydrophillic coatings, as known to those of skill in the art, may also be used. In addition, any of a variety of antithrombogenic coatings, such as heparin, may also be applied to the catheter of the present invention, alone or in combination with other coating types.

Referring to FIGS. 4 and 5, there is illustrated a cross-sectional view of the distal end 14 of catheter 10. Distal end 14 is provided with a soft distal tip 50, which is not pre-formed with tubular body 16, but is instead attached to tubular body 16 as a tube post manufacturing step. Distal tip 50 is preferably soft enough and flexible enough, so as to minimize trauma to body vessels as catheter 10 is advanced, and also to facilitate navigation of catheter 10 in tortuous vessels. In one preferred embodiment, distal tip 50 is formed as a 0.5 cm sleeve of 25-40D Pebax (TM), and is bonded to tubular body 16 by heat fusing. Alternately, distal tip 50 may be attached to tubular body 16 by adhesives, or by insert molding, as is known to those of skill in the art. Preferably, distal tip 50 is in alignment with tubular body 16, and does not bend or curve, such that the radial axis of distal tip 50 is substantially the same as that of tubular body 16.

The distal end 14 of catheter 10 is also preferably provided with a radiopaque material 44. Advantageously, radiopaque material 44 serves as a marker to help the clinician position catheter 10 during a medical procedure. Various well-known radiopaque materials may be used in distal end 14, such as platinum, gold, and platinum-iridium blends. The full length, or part of the length of the tubular body, may also be radiopaque by blending radiopaque materials in the polymeric materials used to form the body. Furthermore, radiopacity of the tip can also be achieved by loading (i.e., comparing) the distal tip 50 with a sufficient amount of barium sulfate. Alternatively, bismuth subcarbonate, bismuth trioxide or bismuth oxychloride may be used as a radiopaque filler. Also, radiopacity may be achieved by using radiopaque wire or flat ribbon to make the braid or coil.

Illustrated in FIGS. 6–9, there is an emboli containment system utilizing catheter 10 of the present invention. Catheter 10 of the present invention is used in the treatment of a stenosis 55 in a lumen 50 in a blood-carrying vessel 58 in which the stenosis 55 at least partially occludes the lumen 50. The emboli containment system depicted in FIG. 6 comprises a catheter 10, as described above, as well as catheters 100 and 200.

Catheter 100 comprises an elongate flexible tubular body 116 having proximal end and distal end 114. An inflatable balloon 126 of the same type as inflatable balloon 26 is coaxially mounted on tubular body 116 on the end 114 of catheter 100. The tubular body 116 has centrally disposed inflation lumen 132 in fluid communication with balloon 126, such that fluid passing through lumen 132 may be used to inflate balloon 126. Alternatively, fluid may be withdrawn from lumen 132 to deflate balloon 126. As shown in FIG. 6, catheter 100 is disposed within main lumen 30 of catheter 10 and is slidably and coaxially mounted therein for variable displacement of balloon 126 with respect to the first balloon 26, as hereinafter described. One preferred embodiment of a catheter 100 is disclosed in our co-pending application, entitled HOLLOW MEDICAL WIRES AND METHODS OF CONSTRUCTING SAME, Ser. No. 08/812,876, filed on the same date as the present application, the entirety of which is incorporated by reference.

The emboli containment system also comprises catheter 200 comprising an elongate flexible tubular body 216 having proximal end and distal end 214. Catheter 200 is also provided with a generally centrally disposed lumen 230 extending from the proximal end to the distal end of catheter 200, and through which catheter 100 is coaxially and slidably mounted.

The distal end 214 of catheter 200 is provided with means for performing a medical procedure, such as an apparatus for treating stenotic lesion 55. In the embodiment of the invention shown in FIG. 6, this means comprises a dilation balloon 226, which is preferably a non-compliant inflatable balloon which is coaxially mounted on the distal end 214 of catheter 200. Balloon 226 may also be attached to tubular body 216 in the same manner as balloons 26 and 126 hereinbefore described. Tubular body 216 is provided with a balloon inflation lumen 232 which is in fluid communication with balloon 226, such that balloon 226 may be inflated by the passage of fluid through lumen 232.

The operation and use of the emboli containment system utilizing the catheter of the present invention for treating occluded vessels may now be briefly described in connection with an occlusion formed by a stenosis in a carotid artery, as illustrated in FIGS. 10A–E.

Catheter 100 is inserted into an incision into a femoral artery of a patient and is advanced through that artery into the aorta of the patient and into the ostium of the carotid artery to be treated. After catheter 100 has been introduced, catheters 10 and 200, with balloons 26 and 226 completely deflated, are introduced over catheter 100 and are advanced into the ostium of the carotid artery and into the lumen or passageway of the vessel as shown in FIGS. 10A–E.

Figure 10B:
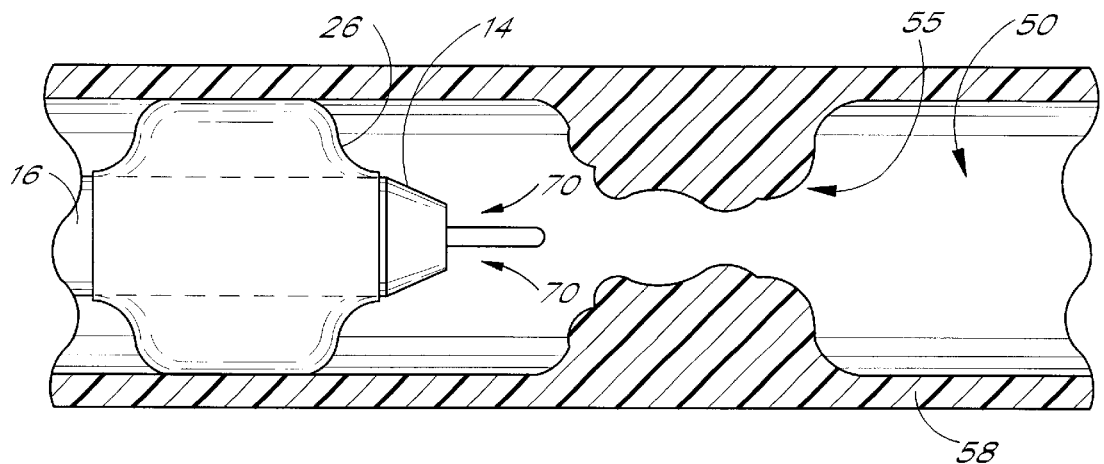

The emboli containment system is advanced until catheter 10 is proximal of a stenosis 55 in the vessel lumen 50 to be treated. Balloon 26 is then inflated by introducing a suitable inflation medium such as a radiopaque liquid into port 18 to cause it to pass through the balloon inflation lumen 32 to inflate balloon 26, as shown in FIG. 10B. Balloon 26 is progressively inflated until it engages the side wall 58 of the vessel to occlude the lumen 50.

Figure 10C:
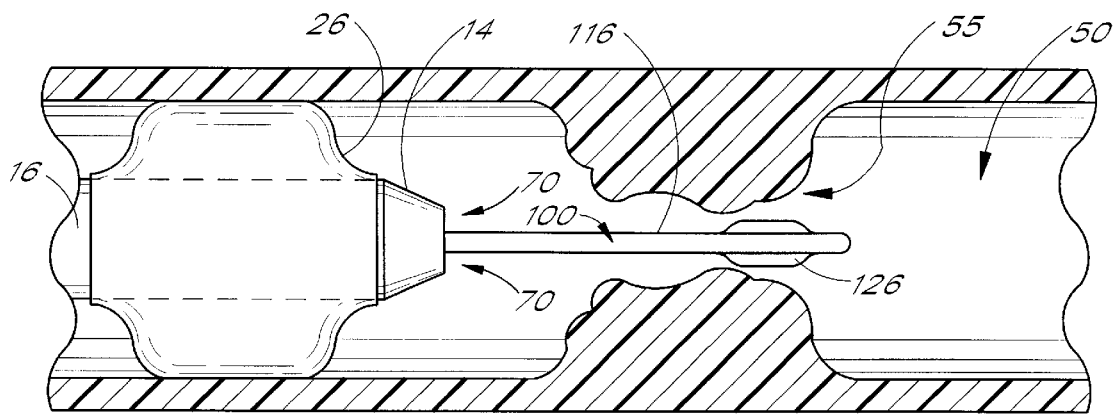
Figure 10D:
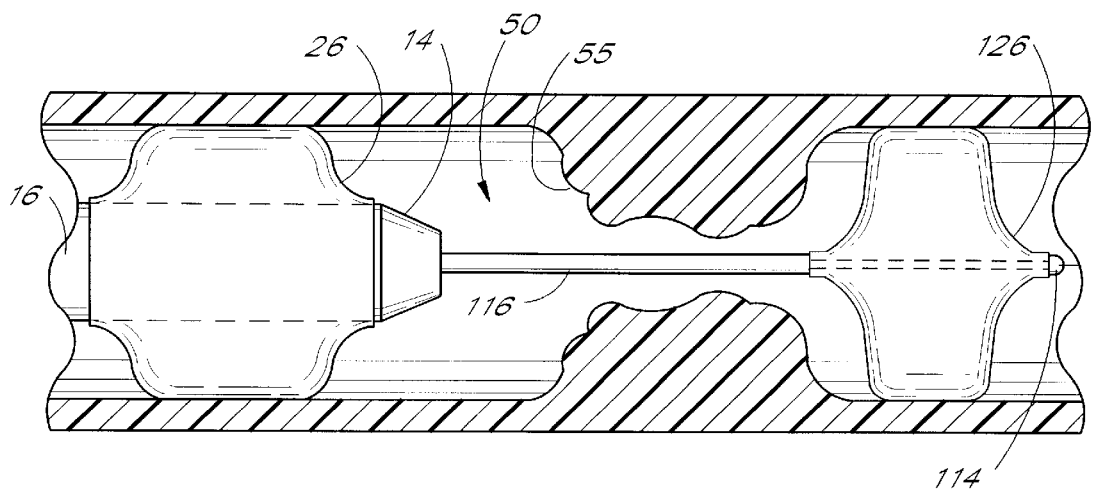
Figure 10E:
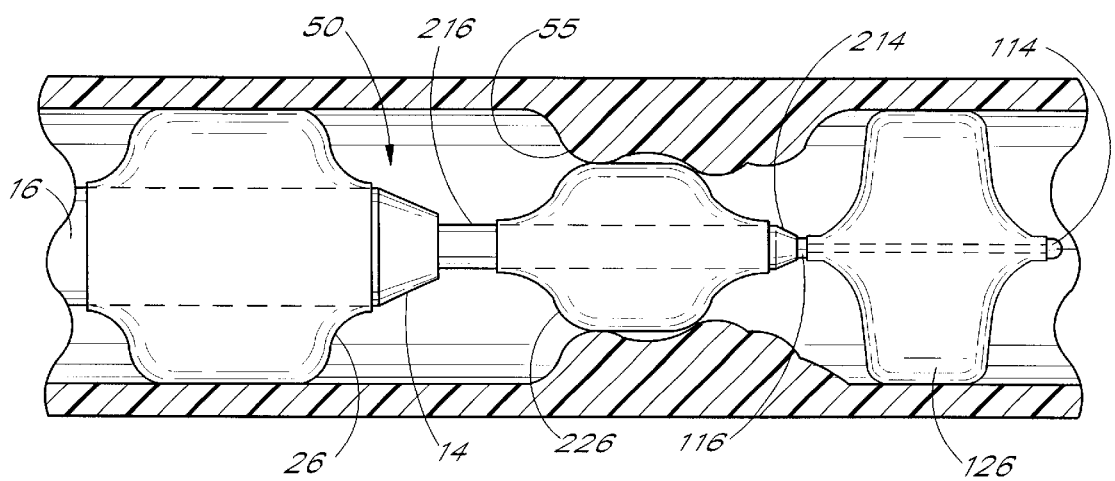

Catheter 100 is then advanced through stenosis 55 as shown in FIG. 10C. Catheter 100 with deflated balloon 126 thereon is advanced through stenosis 55 until the balloon 26 is distal of stenosis 55 as shown in FIG. 10D. Balloon 126 is then inflated by passing an inflation medium through lumen 132 to the interior of the balloon 126 to inflate the balloon 126 until it engages the sidewall 58 of the vessel lumen 50. As soon as the balloon 126 has been inflated, a working space is provided between balloons 26 and 126, so that medical procedures can be undertaken to remove or reduce the stenosis 55 in the space between second balloons 26 and 126, without risk of unwanted particles or emboli escaping into the blood stream.

For emboli containment systems featuring balloon dilation treatment, it is desired to compress the plaque or material forming the stenosis to provide a larger vessel. Thus, catheter 200 is advanced over catheter 100 to cause distal end 214 with balloon 226 thereon to be advanced into the working space. As soon as balloon 226 has been properly positioned within stenosis 55, balloon 226 is inflated with a suitable inflation medium, as for example a radiopaque liquid. Balloon 226 can be inflated to the desired pressure to cause compression of the plaque of the stenosis 55 against the sidewall 58 of lumen 50 by the application of appropriate inflation pressure. As in conventional angioplasty procedures, balloon 226 can be formed of a non-elastic relatively non-compliant material so that appropriate pressures, such as 10–15 atmospheres, can be used within balloon 226 to apply compressive forces to the vessel without danger of rupturing the vessel. It should be appreciated that the non-elastic capabilities can also be achieved by a composite elastic material.

Once the clinician is satisfied that the occlusion forming stenosis 55 has been sufficiently compressed, balloon 226 can be deflated. After the appropriate dilation of stenosis 55 has been accomplished, catheter 200 can be removed from the stenosis. Moreover, in one preferred method, catheter 200 is completely withdrawn from the emboli containment system, and an irrigation catheter is inserted over catheter 100 and through lumen 30, as described in our copending application entitled METHOD FOR EMBOLI CONTAINMENT, Ser. No. 80/812,875 filed on the same date as the present application, the entirety of which is incorporated by reference. Fluid introduced into the working space may be removed by supplying a negative pressure or suction to aspiration port 20. This creates a negative pressure within space 30a defined by the interior surface of lumen 30 and outer tubular body 216, to suck or aspirate blood or other fluids in lumen 50 into space 30a and out of aspiration port 20. In this manner, irrigation and aspiration of the working space may take place so that any plaque coming off the occlusion forming the stenosis 55 can be aspirated out of the vessel. Subsequently, balloon 26 and balloon 126 can be deflated to permit normal blood flow through the vessel lumen 50. The entire catheter assembly can then be removed and a suture applied to the incision created to obtain access to the femoral artery.

It will be appreciated that certain variations of the present invention may suggest themselves to those skilled in the art. The foregoing detailed description is to be clearly understood as given by way of illustration, the spirit and scope of this invention being limited solely by the appended claims.

What is claimed is:

1. A catheter adapted for use in the vasculature of a patient, comprising:
   an elongate body having a distal section and a proximal section, said body having a substantially continuous cross-sectional profile of not greater than about 0.135 inches; and
   an occlusive device mounted on the distal section of said body, said occlusive device comprising an occlusion balloon coupled thereto and having an activated state for embolic containment and a deactivated state having a lower cross-sectional profile not substantially greater than said cross-sectional profile of said body;
   said body comprising:
      an inner structure defining a main lumen for slidably accommodating other vascular catheters and the like, said main lumen having a diameter of about 0.05 inches to about 0.12 inches and having a side wall, said side wall characterized by an absence of perforations therethrough;
      stiffener material arranged over said inner structure;
      an outer peripheral structure surrounding said inner structure and said stiffener material; and
      an elongate hollow structure defining a secondary lumen for passing inflation media to said occlusive balloon to activate said balloon, said elongate hollow structure inserted within said outer perimeter structure and over said stiffener material so as to be in side-by-side arrangement with said inner structure to provide additional stiffening thereto, all of said structures being bonded together to form said body, said secondary lumen having a major axis and a minor axis;
   said secondary lumen having a proximal section and a distal section, said proximal section having a substantially tubular cross-sectional profile of about 0.008 inches to about 0.018 inches and said distal section having a lower non-circular, substantially oval cross-sectional profile in the vicinity of and proximal to said occlusive device, wherein a ratio of the secondary lumen major axis to the secondary lumen minor axis in the distal section of said catheter is greater than a ratio of the secondary lumen major axis to the secondary lumen minor axis in the proximal section of said catheter, and whereby said catheter has a substantially continuous cross-sectional profile.

2. The catheter of claim 1, wherein said inner structure, said outer peripheral structure and said elongate hollow structure each comprise an elongate tube.

3. The catheter of claim 1, wherein said main lumen and said secondary lumen are arranged in a side-by-side arrangement such that the cross-sectional profile of said catheter is substantially tear-drop shaped.

4. The catheter of claim 1, wherein the cross-sectional profile of said catheter body has an eccentricity represented by said secondary lumen.

5. The catheter of claim 1 additionally comprising an inflation port in the proximal section of the body, the inflation port being in fluid communication with the secondary lumen.

6. The catheter of claim 1 additionally comprising a lubricous liner within the main lumen.

7. The catheter of claim 1, wherein the stiffener material comprises a metallic member.

8. The catheter of claim 7, wherein the metallic member comprises a fine wire having a diameter of about 0.0005 inches to about 0.005 inches.

9. The catheter of claim 7, wherein the metallic member comprises a flat ribbon having a thickness of about 0.0005 inches to about 0.005 inches.

10. The catheter of claim 1, wherein a perimeter of the secondary lumen remains constant along the length of the secondary lumen.

11. The catheter of claim 1, wherein the secondary lumen ratio in the distal section is greater than one.

12. The catheter of claim 1, wherein the secondary lumen additionally comprises a transition section between the proximal section and the distal section, and the secondary lumen ratio in the transition section is greater than the secondary lumen ratio in the proximal section, but less than the secondary lumen ratio in the distal section.

13. A catheter, comprising:
   an elongate body having a distal section and a proximal section, said body having a substantially continuous cross-sectional profile; and
   an occlusion device mounted on the distal section of said body, said occlusion device comprising an occlusive balloon coupled thereto;
   said body comprising:
      an inner structure defining a main lumen for accommodating other vascular catheters and the like;
      stiffener material arranged over said inner structure;
      an outer perimeter structure surrounding said inner structure and said stiffener material;
      an elongate hollow structure defining a secondary lumen for passing inflation media to said occlusive balloon to activate said balloon;
   said secondary lumen having a proximal section and a distal section, said proximal section having a substantially tubular cross-sectional profile and said distal section having a lower cross-sectional profile in the vicinity of and proximal to said occlusion device, whereby said catheter has a substantially continuous cross-sectional profile; and
   wherein a ratio of a major axis of the secondary lumen to a minor axis of the secondary lumen in the distal section is greater than a ratio of a major axis of the secondary lumen to a minor axis of the secondary lumen in the proximal section.

14. The catheter of claim 13 additionally comprising an inflation port in the proximal section of the body, the inflation port being in fluid communication with the secondary lumen.

15. The catheter of claim 13 additionally comprising an aspiration port in the proximal section of the body, the aspiration port being in fluid communication with the main lumen.

16. The catheter of claim 13, wherein the balloon is formed of a block copolymer of styrene-ethylene-butylene-styrene.

17. The catheter of claim 13, wherein the stiffener material comprises a metallic member.

18. The catheter of claim 17, wherein the metallic member comprises a metal selected from the group consisting of stainless steel, nitinol, platinum, gold, ELGILOY, and combinations thereof.

19. The catheter of claim 17, wherein the metallic member comprises a metallic braid.

20. The catheter of claim 17, wherein the metallic member comprises a metallic coil.

21. The catheter of claim 13, wherein a cross-sectional profile of the inner structure remains substantially constant along the length of the body.

22. The catheter of claim 13, wherein the secondary lumen has a non-circular, substantially oval-shaped cross-sectional profile in the vicinity of said occlusion device.

23. The catheter of claim 22, wherein the main lumen is not perforated.

24. A catheter, comprising:
   an elongate body having a distal section and a proximal section; and
   an occlusive device mounted on the distal section of said body, said occlusive device having an activated state for embolic containment and a lower profile deactivated state;
   said body comprising:
      an inner lumen for slidably accommodating other vascular catheters and the like;
      a secondary lumen for passing inflation media to said occlusive device to activate said device, said secondary lumen having a major axis and a minor axis, said inner lumen and secondary lumen being disposed in a side-by-side arrangement;
   said secondary lumen having a proximal section and a distal section, said proximal section having a substantially tubular cross-sectional profile and said distal section having a lower cross-sectional profile in the vicinity of said occlusive device, wherein the secondary lumen major axis is greater than the secondary lumen minor axis in the distal section.

25. The catheter of claim 24, wherein the occlusive device comprises a balloon.

26. The catheter of claim 24, wherein the occlusive device comprises a filter.

27. The catheter of claim 24, wherein the occlusive device comprises a braid.

28. The catheter of claim 24, wherein the secondary lumen is adapted to pass activation media for activating said occlusive device.

29. The catheter of claim 28, wherein the activation media comprises inflation fluid.

30. The catheter of claim 28, wherein the activation media comprises a pull wire.

31. The catheter of claim 24, wherein the main lumen is adapted to receive two or more separate catheters which are slidably disposed therein.

32. The catheter of claim 24, wherein the distal section of the body is more flexible than the proximal section of the body.

33. The catheter of claim 24 additionally comprising a lubricous liner within the main lumen.

34. The catheter of claim 33, wherein the lubricous liner is comprised of polytetrafouoroethylene.

35. The catheter of claim 24, wherein the body has an outer surface having a hydrophilic coating.

36. The catheter of claim 24, wherein the body has an outer surface having a hydrophobic coating.

37. The catheter of claim 24, wherein a perimeter of the secondary lumen remains constant along the length of the secondary lumen.

38. The catheter of claim 37, wherein the main lumen is not perforated.

39. The catheter of claim 24, wherein the secondary lumen has a non-circular, substantially oval-shaped cross-sectional profile in the vicinity of said occlusion device.

40. The catheter of claim 24, wherein a ratio of the secondary lumen major axis to the secondary lumen minor axis in the distal section is greater than 1.

41. The catheter of claim 24, wherein the secondary lumen additionally comprises a transition section between the proximal section and the distal section, and a ratio of the major axis to the minor axis in the transition section is greater than the ratio in the proximal section, but less than the ratio in the distal section.

42. The catheter of claim 41, wherein the ratio in the proximal section is about 1.

43. A catheter, comprising:
an elongate body having a distal section and a proximal section, said body having a substantially continuous eccentric cross-sectional profile; and
an occlusion device mounted on the distal section of said body;
said body comprising:
an inner structure defining a main lumen having a relatively large cross-sectional profile; and
an elongate hollow structure defining a secondary lumen, wherein the perimeter of the secondary lumen is substantially constant along substantially the entire length of said secondary lumen, said secondary lumen having a first cross-sectional profile in said proximal section of said body and a differently-shaped, second cross-sectional profile in said distal section of said body in the vicinity of said occlusion device;
said structures arranged so as to be in a side-by-side arrangement such that said elongate hollow structure provides a stiffener for said inner structure.

44. The catheter of claim 43, wherein the cross-sectional profile of said body is substantially tear-drop shaped.

45. The catheter of claim 43, wherein said body has a cross-sectional profile which is dominated by a tubular cross-sectional profile, represented by said main lumen.

46. The catheter of claim 43, wherein the occlusive device comprises a balloon.

47. The catheter of claim 43, wherein the occlusive device comprises a filter.

48. The catheter of claim 43, wherein the occlusive device comprises a braid.

49. The catheter of claim 43 in combination with a second catheter, the second catheter including a second elongate body having proximal and distal ends and having a therapeutic device disposed on the distal end, and the second catheter is adapted to be slidably movable within the main lumen.

50. The catheter of claim 43, wherein the main lumen is adapted to receive two or more separate catheters which are slidably disposed therein.

51. The catheter of claim 43, wherein the first cross-sectional profile is substantially circular and the second cross-sectional profile is non-circular and substantially oval-shaped.

52. The catheter of claim 51, wherein the secondary lumen has a major axis and a minor axis, and a ratio of the major axis to the minor axis at the second cross-sectional profile is greater than the ratio at the first cross-sectional profile.

53. The catheter of claim 43, wherein a first side of said hollow structure is adjacent said inner structure and a second side of said hollow structure is opposite said first side, and a distance between the first and second sides is greater in the proximal section of said body than in the vicinity of said occlusive device.

54. The catheter of claim 43, wherein the distal section of the body is more flexible than the proximal section of the body.

* * * * *